(12) United States Patent
Shen

(10) Patent No.: US 12,029,904 B2
(45) Date of Patent: Jul. 9, 2024

(54) ELECTROENCEPHALOGRAPH DEVICE AND SYSTEM, COMPUTER DEVICE, AND STORAGE MEDIUM

(71) Applicant: NEURACLE TECHNOLOGY (CHANGZHOU) CO., LTD., Jiangsu (CN)

(72) Inventor: Wei Shen, Jiangsu (CN)

(73) Assignee: NEURACLE TECHNOLOGY (CHANGZHOU) CO., LTD., Jiangsu (CN)

( * ) Notice: Subject to any disclaimer, the term of this patent is extended or adjusted under 35 U.S.C. 154(b) by 0 days.

(21) Appl. No.: 18/272,806

(22) PCT Filed: Jun. 10, 2021

(86) PCT No.: PCT/CN2021/099399
§ 371 (c)(1),
(2) Date: Jul. 18, 2023

(87) PCT Pub. No.: WO2022/160557
PCT Pub. Date: Aug. 4, 2022

(65) Prior Publication Data
US 2024/0075287 A1 Mar. 7, 2024

(30) Foreign Application Priority Data

Jan. 27, 2021 (CN) .......................... 202110106891.9

(51) Int. Cl.
*A61N 1/36* (2006.01)
(52) U.S. Cl.
CPC ............................... *A61N 1/36031* (2017.08)
(58) Field of Classification Search
CPC ............ A61N 1/36025; A61N 1/36028; A61N 1/36075–36107; A61B 5/375–384
See application file for complete search history.

(56) References Cited

U.S. PATENT DOCUMENTS

2009/0319004 A1 12/2009 Sabel
2021/0325836 A1* 10/2021 Sepe ...................... G06N 5/048

FOREIGN PATENT DOCUMENTS

CN 104874102 9/2015
CN 106407733 2/2017
(Continued)

OTHER PUBLICATIONS

"International Search Report (Form PCT/ISA/210) of PCT/CN2021/099399", mailed on Oct. 27, 2021, with English translation thereof, pp. 1-6.

*Primary Examiner* — George R Evanisko
(74) *Attorney, Agent, or Firm* — JCIPRNET

(57) ABSTRACT

The present disclosure relates to the technical field of electronic medical treatment, and provides an electroencephalograph device and system, a computer device, and a storage medium. The electroencephalograph device includes: a stimulation unit, configured for generating a stimulation signal; and an acquisition unit, configured for acquiring physiological electrical signals of a human brain. The acquiring, by the acquisition unit, the physiological electrical signals of the human brain includes: when the stimulation unit does not apply the stimulation signal to a human body, acquiring, by the acquisition unit, the physiological electrical signals of the human brain according to a first acquisition parameter; and when the stimulation unit applies the stimulation signal to the human body, acquiring, by the acquisition unit, the physiological electrical signals of the human brain according to a second acquisition parameter, the first acquisition parameter being different from the second acquisition parameter.

15 Claims, 8 Drawing Sheets

(56) References Cited

FOREIGN PATENT DOCUMENTS

| | | |
|---|---|---|
| CN | 109009887 | 12/2018 |
| CN | 109464131 | 3/2019 |
| CN | 110720900 | 1/2020 |
| CN | 112445343 | 3/2021 |
| WO | 2016097937 | 6/2016 |

* cited by examiner

ELECTROENCEPHALOGRAPH DEVICE AND SYSTEM, COMPUTER DEVICE, AND STORAGE MEDIUM

CROSS-REFERENCE TO RELATED APPLICATION

This application is a 371 of international application of PCT application serial no. PCT/CN2021/099399, filed on Jun. 10, 2021, which claims the priority benefit of China application no. 202110106891.9, filed on Jan. 27, 2021. The entirety of each of the above-mentioned patent applications is hereby incorporated by reference herein and made a part of this specification.

BACKGROUND

Technical Field

The present disclosure relates to the technical field of electronic medical treatment, and in particular, to an electroencephalograph device and system, a computer device, and a storage medium.

Description of Related Art

As part of the basic physiological signals of the human body, the physiological electrical signals of the brain provide important references for clinical diagnosis and treatment. However, it is rather difficult to study the physiological electrical signals of the brain due to their non-stationary randomness.

The electrical stimulation therapy plays an important role in scientific research and medical treatment and is critical to the study of the physiological electrical signals of the brain. This therapy works well in treating common diseases such as epilepsy by applying specific electrical stimulation to a targeted part of the human body and analyzing the fed-back electroencephalogram signals. The electrical stimulation applied to the human body may be conducted by means of a direct current, an alternating current, or the like, and the electrical stimulation signal will introduce certain noise into the electroencephalogram signal.

However, the noise introduced during stimulation will lead to signal aliasing and signal saturation, and the noise aliasing and saturation have a great impact on the acquisition of the physiological electrical signals of the brain during stimulation. How to acquire effective electroencephalogram data during stimulation has long puzzled researchers in scientific research and medical treatment. The failure in acquisition of clean electroencephalogram data during stimulation hinders further study on some important projects and medical research such as basic research about the impact of stimulation on the brain, for example, practical medical research about the impact analysis of Parkinson's patients taking deep brain stimulation (DBS) electronic drugs and chemical drugs.

Therefore, how to acquire effective electroencephalogram data during stimulation has become a technical problem in urgent need of solutions in this field.

SUMMARY

To solve the above technical problem, the present disclosure provides a technical solution of acquiring effective electroencephalogram data during stimulation.

In one aspect, an embodiment of the present disclosure provides an electroencephalograph device, which includes:
a stimulation unit, configured for generating a stimulation signal and apply the stimulation signal to a human body; and
an acquisition unit, configured for acquiring physiological electrical signals of a human brain, where
the acquiring, by the acquisition unit, the physiological electrical signals of the human brain includes: when the stimulation unit does not apply the stimulation signal to the human body (during non-stimulation), acquiring, by the acquisition unit, the physiological electrical signals of the human brain according to a first acquisition parameter; and when the stimulation unit applies the stimulation signal to the human body (during stimulation), acquiring, by the acquisition unit, the physiological electrical signals of the human brain according to a second acquisition parameter, the first acquisition parameter being different from the second acquisition parameter.

According to the embodiment of the present disclosure, the acquisition unit acquires the physiological electrical signals of the brain by using different acquisition parameters during stimulation and non-stimulation, so as to reduce the influence of noise aliasing and signal saturation on the acquired electroencephalogram signals during stimulation, thereby acquiring effective electroencephalogram data.

In some embodiments of the present disclosure, the first acquisition parameter includes a first acquisition frequency and/or a first signal gain; and the second acquisition parameter includes a second acquisition frequency and/or a second signal gain, the first acquisition frequency being lower than the second acquisition frequency and the second signal gain being lower than the first signal gain.

In some embodiments of the present disclosure, the electroencephalograph device further includes a storage unit configured for storing the first acquisition parameter and the second acquisition parameter. Alternatively, the acquisition unit includes the storage unit.

According to the embodiment of the present disclosure, the acquisition unit adjusts the acquisition parameters according to the prestored parameters, so as to acquire the physiological electrical signals of the brain by using different parameters during non-stimulation and stimulation.

In some embodiments of the present disclosure, the acquiring, by the acquisition unit, the physiological electrical signals of the human brain further includes: when the acquisition unit determines that the stimulation unit intends to apply stimulation, adjusting, by the acquisition unit, the acquisition frequency into the second acquisition frequency, where
when the stimulation unit applies the stimulation signal to the human body, the acquiring, by the acquisition unit, the physiological electrical signals of the human brain according to the second acquisition parameter includes: judging, by the acquisition unit, whether an amplitude of the acquired signals exceeds a set threshold; and if yes, adjusting, by the acquisition unit, the signal gain into the second signal gain.

In some embodiments of the present disclosure, the determining, by the acquisition unit, that the stimulation unit intends to apply stimulation includes:
determining, by the acquisition unit, to request the stimulation unit to apply stimulation according to the acquired physiological electrical signals of the brain; or
determining, by the acquisition unit, that the stimulation unit intends to apply stimulation after the acquisition unit receives a notification of the stimulation, where the notification is sent by the stimulation unit or by a device other than the acquisition unit and the stimulation unit.

According to the embodiment of the present disclosure, the acquisition unit adjusts the acquisition parameters during stimulation in real time according to the acquired signals, so as to acquire the physiological electrical signals of the brain by using different parameters during non-stimulation and stimulation.

In another aspect, an embodiment of the present disclosure provides an electroencephalograph system, which includes:
a stimulation unit, configured for generating a stimulation signal and apply the stimulation signal to a human body;
an acquisition unit, configured for acquiring physiological electrical signals of a human brain; and
a control unit, configured for controlling the acquisition unit to acquire the physiological electrical signals of the human brain according to a first acquisition parameter when the stimulation unit does not apply the stimulation signal to the human body (during non-stimulation); and control the acquisition unit to acquire the physiological electrical signals of the human brain according to a second acquisition parameter when the stimulation unit applies the stimulation signal to the human body (during stimulation), the first acquisition parameter being different from the second acquisition parameter.

According to the embodiment of the present disclosure, the control unit controls the acquisition unit to acquire the physiological electrical signals of the brain by using different acquisition parameters during stimulation and non-stimulation, so as to reduce the influence of noise aliasing and signal saturation on the acquired electroencephalogram signals during stimulation, thereby acquiring effective electroencephalogram data.

In some embodiments of the present disclosure, the first acquisition parameter includes a first acquisition frequency and/or a first signal gain; and the second acquisition parameter includes a second acquisition frequency and/or a second signal gain, the first acquisition frequency being lower than the second acquisition frequency and the second signal gain being lower than the first signal gain.

In some embodiments of the present disclosure, the electroencephalograph system further includes a storage unit configured for storing the first acquisition parameter and the second acquisition parameter. Alternatively, the control unit includes the storage unit.

According to the embodiment of the present disclosure, the control unit adjusts the acquisition parameters of the acquisition unit according to the prestored parameters, so as to enable the acquisition unit to acquire the physiological electrical signals of the brain by using different parameters during non-stimulation and stimulation.

In some embodiments of the present disclosure, the control unit is further configured for adjusting the acquisition frequency of the acquisition unit into the second acquisition frequency when the control unit determines that the stimulation unit intends to apply stimulation, where
when the stimulation unit applies the stimulation signal to the human body, the controlling, by the control unit, the acquisition unit to acquire the physiological electrical signals of the human brain according to the second acquisition parameter includes: judging whether an amplitude of the acquired signals exceeds a set threshold; and if yes, adjusting the signal gain of the acquisition unit into the second signal gain.

In some embodiments of the present disclosure, the determining, by the control unit, that the stimulation unit intends to apply stimulation includes:
determining, by the control unit, to request the stimulation unit to apply stimulation according to the physiological electrical signals of the brain acquired by the acquisition unit; or
determining, by the control unit, that the stimulation unit intends to apply stimulation after the control unit receives a notification of the stimulation, where the notification is sent by the stimulation unit or by a device other than the acquisition unit, the stimulation unit, and the control unit.

According to the embodiment of the present disclosure, the control unit adjusts the acquisition parameters during stimulation in real time according to the acquired signals, so as to acquire the physiological electrical signals of the brain by using different parameters during non-stimulation and stimulation.

In yet another aspect, an embodiment of the present disclosure provides a computer readable storage medium configured for storing computer readable instructions, where a processor executes the computer readable instructions to perform the following steps:
judging whether the stimulation unit applies the stimulation signal to the human body;
when the stimulation unit does not apply the stimulation signal to the human body, acquiring, by the acquisition unit, the physiological electrical signals of the human brain according to the first acquisition parameter; and
when the stimulation unit applies the stimulation signal to the human body, acquiring, by the acquisition unit, the physiological electrical signals of the human brain according to the second acquisition parameter,
the first acquisition parameter being different from the second acquisition parameter.

In some embodiments of the present disclosure, the first acquisition parameter includes the first acquisition frequency and/or the first signal gain; and the second acquisition parameter includes the second acquisition frequency and/or the second signal gain, the first acquisition frequency being lower than the second acquisition frequency and the second signal gain being lower than the first signal gain.

In some embodiments of the present disclosure, the processor executes the computer readable instructions to perform the following steps:
when determining that the stimulation unit intends to apply stimulation, adjusting the acquisition frequency of the acquisition unit into the second acquisition frequency; and
when the stimulation unit applies the stimulation signal to the human body, judging whether the amplitude of the acquired signals exceeds the set threshold; and if yes, adjusting the signal gain of the acquisition unit into the second signal gain.

In some embodiments of the present disclosure, the determining that the stimulation unit intends to apply stimulation includes:
determining to request the stimulation unit to apply stimulation according to the physiological electrical signals of the brain acquired by the acquisition unit; or
determining that the stimulation unit intends to apply stimulation according to a received notification of the stimulation.

In still another aspect, an embodiment of the present disclosure provides a computer device including a memory and a processor. The memory includes the computer readable storage medium. The processor is configured for executing the computer readable instructions stored in the memory to perform the processes, operations, and steps described in the above embodiments.

According to the aspects of the present disclosure, the technical solution proposed by the present disclosure adaptively increases the acquisition frequency and reduces the signal gain during stimulation without manual intervention, which effectively reduces the influence of noise aliasing and signal saturation on the physiological electrical signals of the brain during stimulation under the condition of continuous acquisition, thereby ensuring high readability of the physiological electrical signals of the brain. Therefore, it is ensured that all the acquired physiological electrical signals of the brain meet the needs of scientific research and medical treatment.

DESCRIPTION OF THE EMBODIMENTS

The present disclosure will be illustrated in detail below with reference to the accompanying drawings and specific embodiments. The well-known components, modules, and units as well as their mutual connections, links, communications, or operations are not shown or described in detail. The stated features, structures, or functions can be combined in any way in one or more embodiments. Persons skilled in the art should understand that the embodiments described below are merely for illustration, instead of limiting the protection scope of the present disclosure. It can also be easily understood that the modules or units or the processing methods in the embodiments described herein and shown in the accompanying drawings can be combined and designed based on different configurations.

Figure 1:
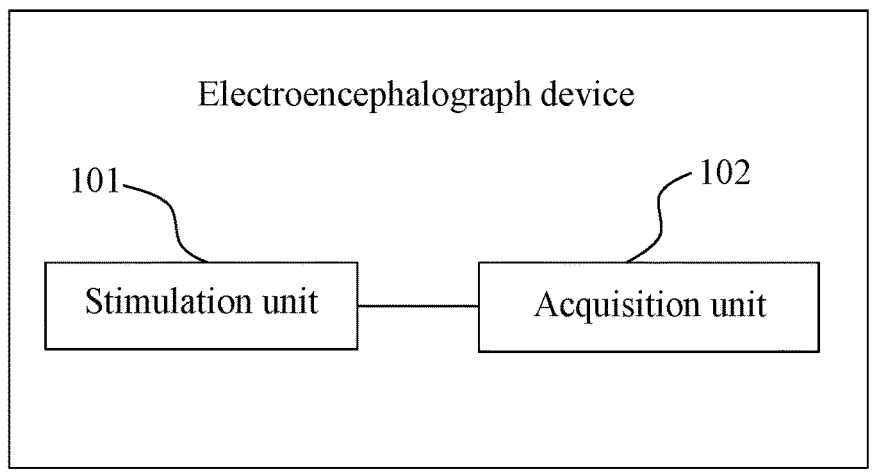
FIG. 1 is a schematic block diagram of an electroencephalograph device according to an embodiment of the present disclosure.

FIG. 1 shows an electroencephalograph device according to an embodiment of the present disclosure. The electroencephalograph device includes, but is not limited to, a stimulation unit 101 and an acquisition unit 102. The stimulation unit 101 is configured for generating a stimulation signal, for example, alternating current stimulation or pulsed current stimulation, and apply the stimulation signal to a human body, for example, a human brain. In an alternative embodiment of the present disclosure, the stimulation signal further includes auditory stimulation, tactile stimulation, or visual stimulation.

The acquisition unit 102 is configured for acquiring physiological electrical signals of the human brain, including signals in response to the stimulation.

In the embodiment of the present disclosure, the acquiring, by the acquisition unit 102, the physiological electrical signals of the human brain includes: when the stimulation unit 101 does not apply the stimulation signal to the human body (during non-stimulation), acquiring, by the acquisition unit 102, the physiological electrical signals of the human brain according to a first acquisition parameter; and when the stimulation unit 101 applies the stimulation signal to the human body (during stimulation), acquiring, by the acquisition unit 102, the physiological electrical signals of the human brain according to a second acquisition parameter, the first acquisition parameter being different from the second acquisition parameter. The first acquisition parameter includes a first acquisition frequency (that is, sampling rate) and/or a first signal gain; and the second acquisition parameter includes a second acquisition frequency and/or a second signal gain, the first acquisition frequency being lower than the second acquisition frequency and the second signal gain being lower than the first signal gain.

According to the embodiment of the present disclosure, the acquisition unit acquires the physiological electrical signals of the brain by using different acquisition parameters during stimulation and non-stimulation, so as to reduce the influence of noise aliasing and signal saturation on the acquired electroencephalogram signals during stimulation, thereby acquiring effective electroencephalogram data. Examples are given below to illustrate in detail the processing of the electroencephalograph device in the embodiment of the present disclosure.

Example 1

Figure 2:
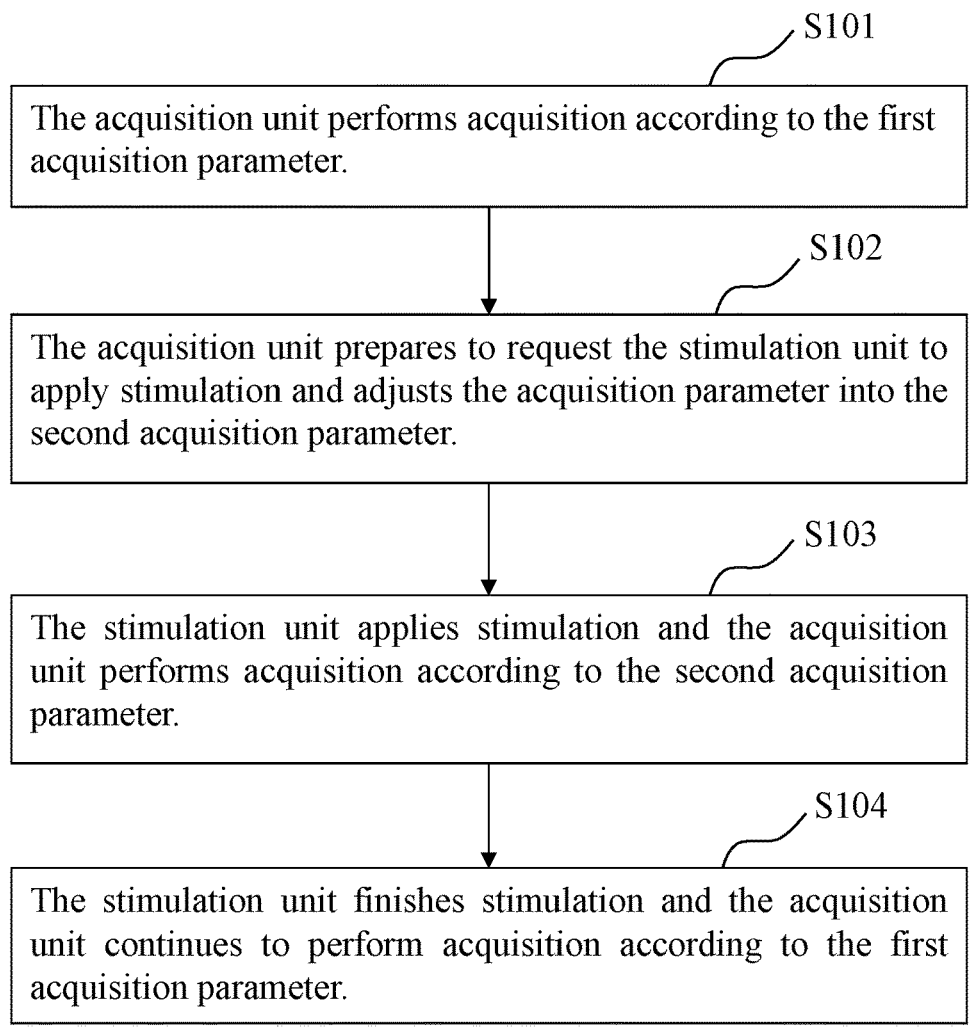
FIG. 2 shows a processing flow according to Example 1 of the present disclosure.

FIG. 2 shows a processing flow according to Example 1 of the present disclosure. In the Example 1, the acquisition unit adjusts the acquisition operations during stimulation and non-stimulation according to the prestored acquisition parameters. Correspondingly, the electroencephalograph device further includes a storage unit configured for storing the first acquisition parameter and the second acquisition parameter. In an alternative embodiment, the acquisition unit includes the storage unit.

In the Example 1, the electroencephalograph device performs the following steps.

S101: When no stimulation is applied (during non-stimulation), the acquisition unit 102 acquires the physiological electrical signals of the human brain according to the prestored first acquisition parameter. For example, the sampling rate (that is, the first acquisition frequency) is 1 kHz and the gain (that is, the first signal gain) is 100.

S102: The acquisition unit 102 prepares to request the stimulation unit 101 to apply stimulation, and adjusts the acquisition parameter into the second acquisition parameter. For example, the sampling rate (that is, the second acquisition frequency) is 16 kHz and the gain (that is, the second signal gain) is 1.

S103: The stimulation unit 101 applies stimulation, and the acquisition unit acquires the physiological electrical signals of the brain according to the adjusted acquisition parameter during stimulation. That is, the physiological electrical signals of the brain are acquired according to the sampling rate of 16 kHz and the signal gain of 1.

S104: The stimulation unit 101 finishes stimulation and during non-stimulation, the acquisition unit 102 restores the acquisition parameter, that is, performs acquisition according to the first acquisition parameter with the sampling rate of 1 kHz and the gain of 100.

It can be seen from the above that, in the Example 1, the acquisition unit 102 initiates the stimulation and adjusts the acquisition parameters used during stimulation and non-stimulation according to the prestored parameters.

Example 2

Figure 3:
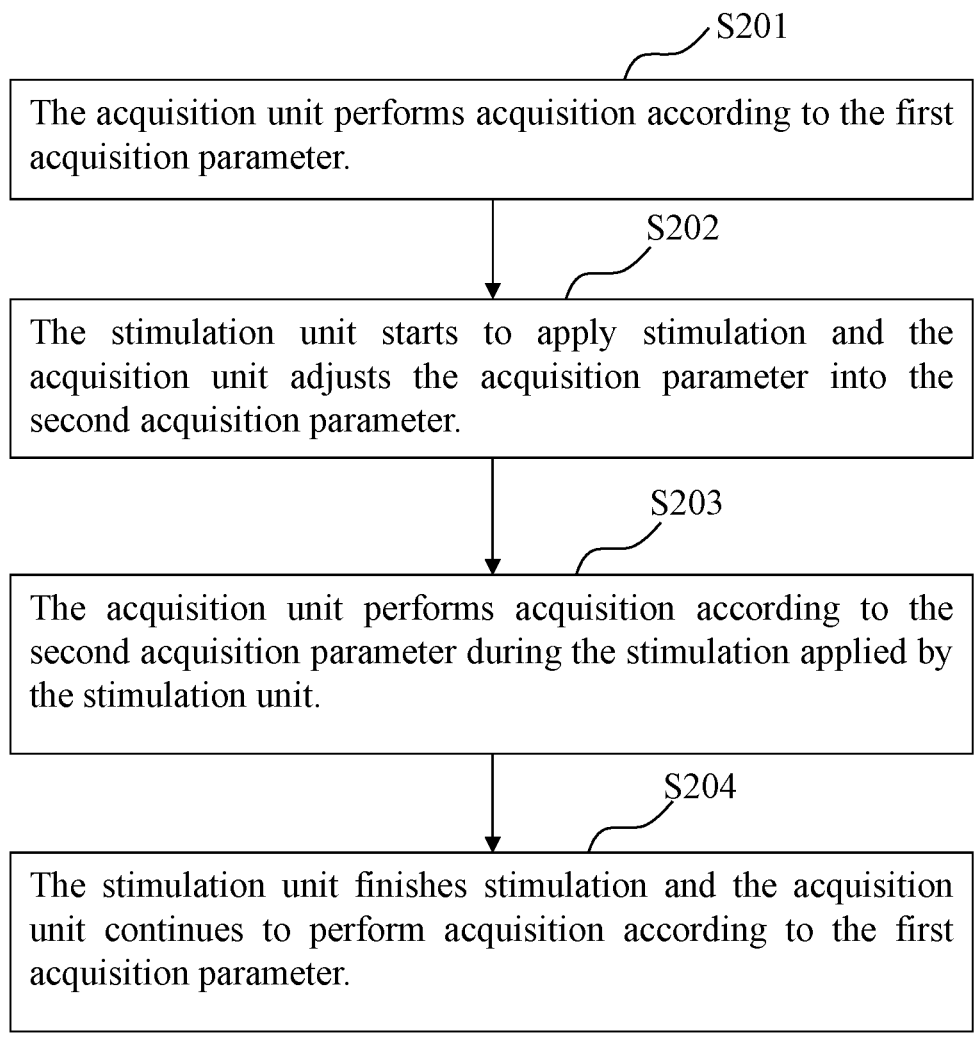
FIG. 3 shows a processing flow according to Example 2 of the present disclosure.

FIG. 3 shows a processing flow according to Example 2 of the present disclosure. The difference between the Example 2 and the Example 1 is that the stimulation unit 101 initiates the stimulation in the Example 2. Specifically, the electroencephalograph device performs the following steps.

S201: When no stimulation is applied (during non-stimulation), the acquisition unit 102 acquires the physiological electrical signals of the human brain according to the prestored first acquisition parameter. For example, the sampling rate (that is, the first acquisition frequency) is 1 kHz and the gain (that is, the first signal gain) is 100.

S202: The stimulation unit 101 starts to apply stimulation and notifies the acquisition unit 102. The acquisition unit 102 receives the stimulation initiation notification from the stimulation unit 101 and adjusts the acquisition parameter into the second acquisition parameter. For example, the sampling rate (that is, the second acquisition frequency) is 16 kHz and the gain (that is, the second signal gain) is 1.

S203: The acquisition unit 102 acquires the physiological electrical signals of the brain according to the adjusted acquisition parameter during the stimulation applied by the stimulation unit 101 to the human body. That is, the physiological electrical signals of the brain are acquired according to the sampling rate of 16 kHz and the signal gain of 1.

S204: The stimulation unit 101 finishes stimulation and during non-stimulation, the acquisition unit 102 restores the acquisition parameter, that is, performs acquisition according to the first acquisition parameter with the sampling rate of 1 kHz and the gain of 100.

It can be seen from the above that, the acquisition unit performs acquisition according to the prestored parameters in the Example 1 and the Example 2. The present disclosure is not limited thereto, and the acquisition parameters can also be adjusted according to real-time feedback. Specifically, when the acquisition unit determines that the stimulation unit intends to apply stimulation, the acquisition unit adjusts the acquisition frequency into the second acquisition frequency. During stimulation, the acquisition unit judges whether the amplitude of the acquired signals exceeds a set threshold; and if yes, the acquisition unit adjusts the signal gain into the second signal gain. The determining, by the acquisition unit, that the stimulation unit intends to apply stimulation includes: determining, by the acquisition unit, to request the stimulation unit to apply stimulation according to the acquired physiological electrical signals of the brain; or determining, by the acquisition unit, that the stimulation unit intends to apply stimulation after the acquisition unit receives a notification of the stimulation. The notification is sent by the stimulation unit or by a device other than the acquisition unit and the stimulation unit. Examples are given below for detailed illustration.

Example 3

Figure 4:
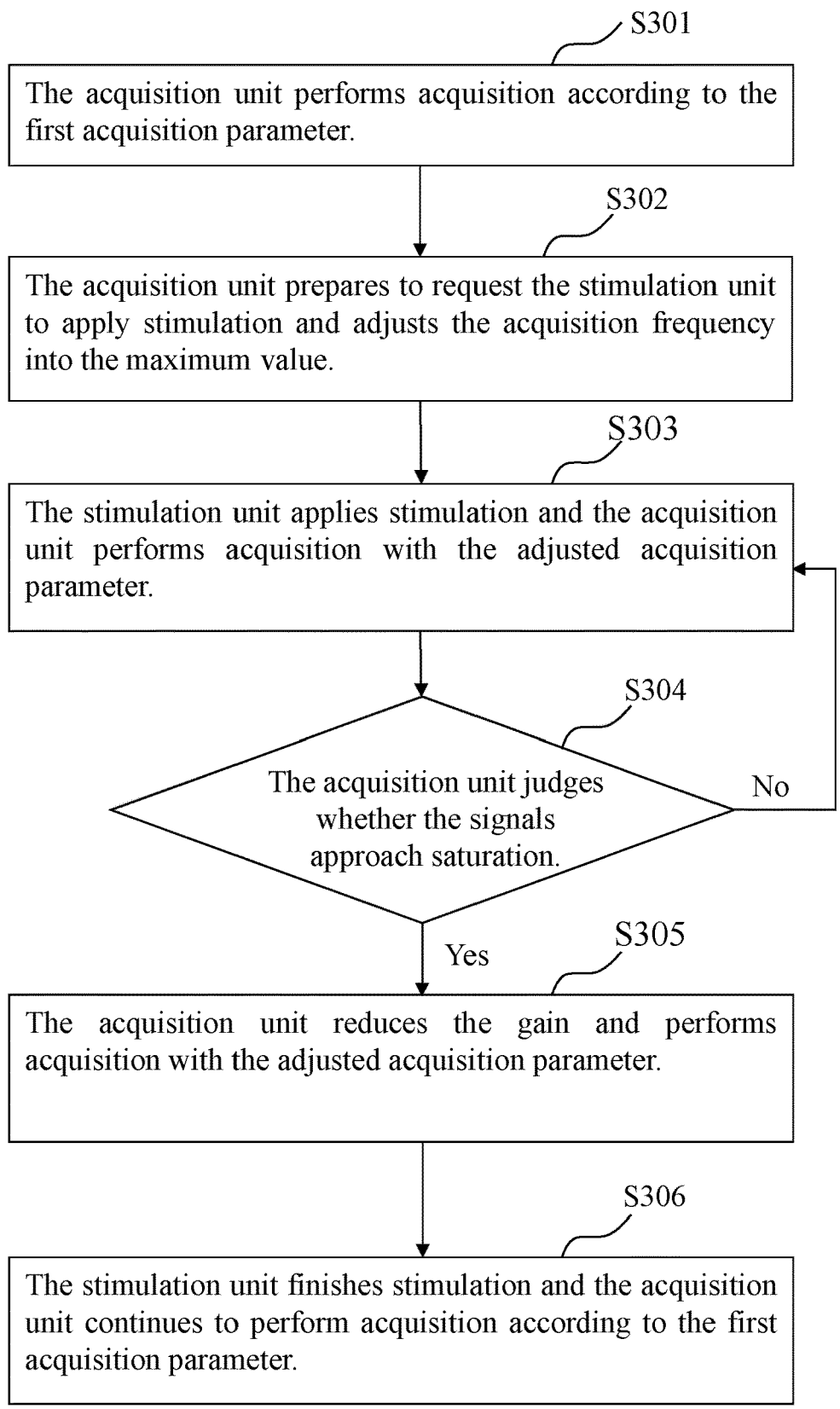
FIG. 4 shows a processing flow according to Example 3 of the present disclosure.

FIG. 4 shows a processing flow according to Example 3 of the present disclosure. In the Example 3, the electroencephalograph device performs the following steps.

S301: When no stimulation is applied (during non-stimulation), the acquisition unit 102 acquires the physiological electrical signals of the human brain according to the first acquisition parameter. For example, the sampling rate (that is, the first acquisition frequency) is 1 kHz and the gain (that is, the first signal gain) is 100.

S302: The acquisition unit 102 prepares to request the stimulation unit 101 to apply stimulation, and adjusts the acquisition frequency into the acquisition frequency of the second acquisition parameter different from the first acquisition parameter. For example, the acquisition frequency is a maximum value supported by the system of the electroencephalograph device. In an alternative embodiment, the acquisition frequency of the second acquisition parameter can be other values higher than the first acquisition frequency.

S303: The stimulation unit 101 starts stimulation as being requested, and the acquisition unit 102 acquires the physiological electrical signals of the brain according to the adjusted acquisition parameter during stimulation. For example, the acquisition is performed with a maximum sampling rate and a gain of 100.

S304: The acquisition unit 102 judges in real time whether the acquired signals approach saturation. For example, the acquisition unit 102 judges whether the signal amplitude exceeds a set threshold. If yes, S305 is performed; otherwise, S303 is performed.

S305: The acquisition unit 102 reduces the signal gain, that is, performs acquisition with a gain lower than 100 (for example, 1) and a maximum sampling rate.

S306: The stimulation unit 101 finishes stimulation and the acquisition unit 102 restores the acquisition parameter, that is, performs acquisition according to the first acquisition parameter.

It can be seen from the above that, in the Example 3, the acquisition unit adjusts the acquisition parameters in real time according to the acquired signals, which also reduces the influence of noise aliasing and signal gain on the acquired signals during stimulation.

Example 4

Figure 5:
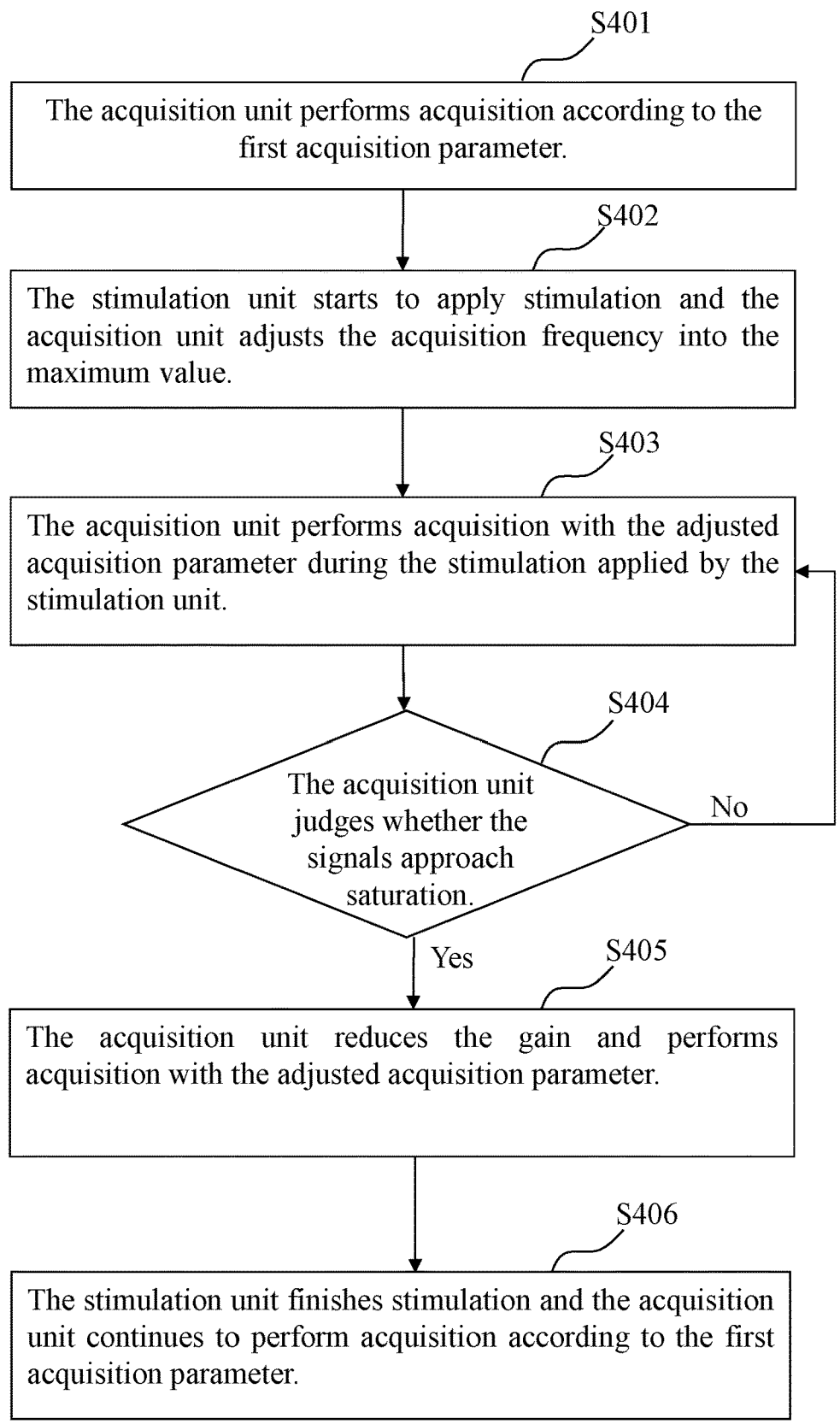
FIG. 5 shows a processing flow according to Example 4 of the present disclosure.

FIG. 5 shows a processing flow according to Example 4 of the present disclosure. The main difference from the Example 3 is that the stimulation unit 101 initiates the stimulation in the Example 4. As shown in FIG. 5, the electroencephalograph device performs the following steps.

S401: When no stimulation is applied (during non-stimulation), the acquisition unit 102 acquires the physiological electrical signals of the human brain according to the first acquisition parameter. For example, the sampling rate (that is, the first acquisition frequency) is 1 kHz and the gain (that is, the first signal gain) is 100.

S402: The stimulation unit 101 starts to apply stimulation and notifies the acquisition unit 102. The acquisition unit 102 receives the notification and adjusts the acquisition frequency into the acquisition frequency of the second acquisition parameter different from the first acquisition parameter. For example, the acquisition frequency is a maximum value supported by the system of the electroencephalograph device. In an alternative embodiment, the acquisition frequency of the second acquisition parameter can be other values higher than the first acquisition frequency.

S403: The acquisition unit 102 acquires the physiological electrical signals of the brain according to the adjusted acquisition parameter during stimulation. For example, the acquisition is performed with a maximum sampling rate and a gain of 100.

S404: The acquisition unit 102 judges in real time whether the acquired signals approach saturation. For example, the acquisition unit 102 judges whether the signal amplitude exceeds a set threshold. If yes, S405 is performed; otherwise, S403 is performed.

S405: The acquisition unit 102 reduces the signal gain, that is, performs acquisition with a gain lower than 100 (for example, 1) and a maximum sampling rate.

S406: The stimulation unit 101 finishes stimulation and the acquisition unit 102 restores the acquisition parameter, that is, performs acquisition according to the first acquisition parameter.

The above examples or embodiments describe the processing of the acquisition unit of the electroencephalograph device without external control. However, in an alternative embodiment, the control operations in the above processing can also be performed by a separate control system.

Figure 6:
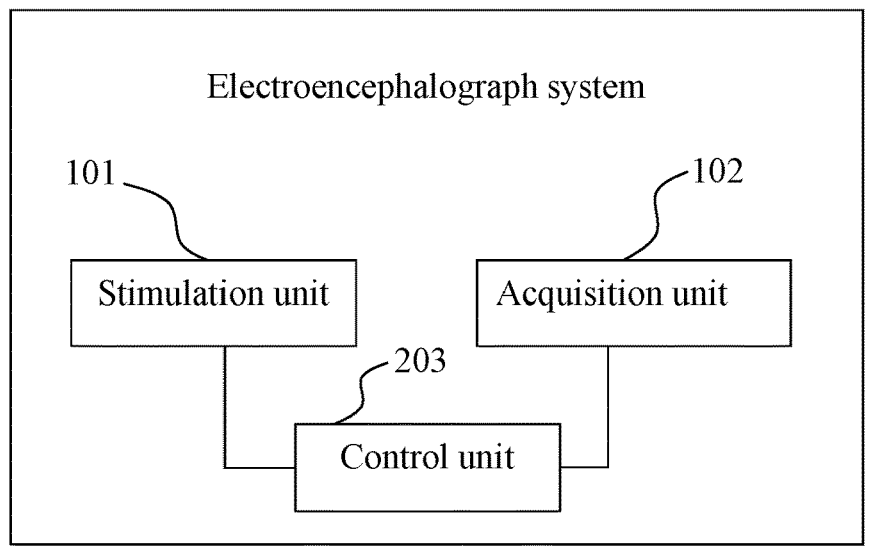
FIG. 6 is a schematic block diagram of an electroencephalograph system according to another embodiment of the present disclosure.

FIG. 6 shows an electroencephalograph system according to another embodiment of the present disclosure. The system includes:

a stimulation unit 101, configured for generating a stimulation signal and apply the stimulation signal to a human body;

an acquisition unit 102, configured for acquiring physiological electrical signals of a human brain; and a control unit 203, configured for controlling the acquisition unit 102 to acquire the physiological electrical signals of the human brain according to a first acquisition parameter when the stimulation unit 101 does not apply the stimulation signal to the human body (during non-stimulation); and control the acquisition unit 102 to acquire the physiological electrical signals of the human brain according to a second acquisition parameter when the stimulation unit 101 applies the stimulation signal to the human body (during stimulation), the first acquisition parameter being different from the second acquisition parameter. For example, the first acquisition parameter includes a first acquisition frequency and/or a first signal gain; and the second acquisition parameter includes a second acquisition frequency and/or a second signal gain, the first acquisition frequency being lower than the second acquisition frequency and the second signal gain being lower than the first signal gain.

In some embodiments of the present disclosure, the stimulation unit 101, the acquisition unit 102, and the control unit 203 are configured in one device. For example, the control unit 203 is configured in the electroencephalograph device shown in FIG. 1. In other embodiments of the present disclosure, the control unit 203 is configured outside the electroencephalograph device shown in FIG. 1, that is, the control unit 203 is an external control system.

Examples are given below to illustrate the processing of the electroencephalograph system in the present disclosure.

Example 5

Figure 7:
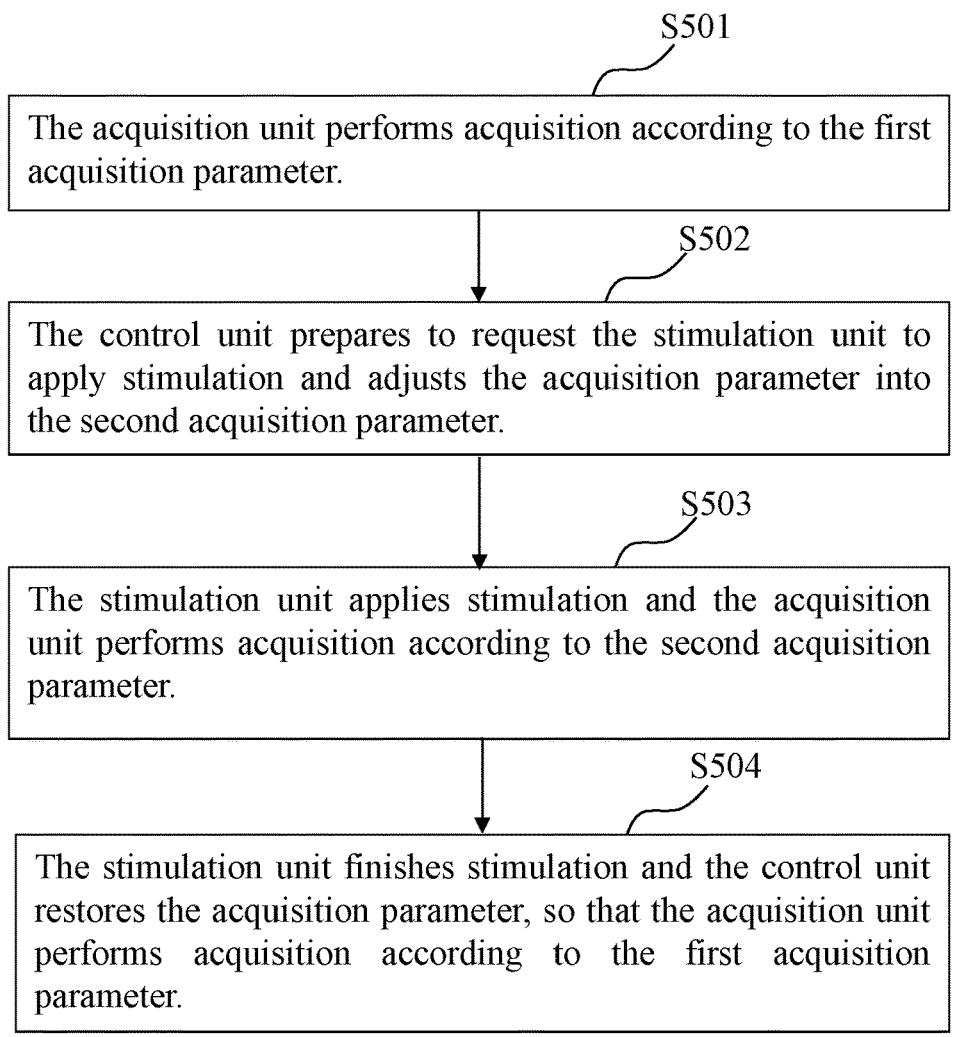
FIG. 7 shows a processing flow according to Example 5 of the present disclosure.

FIG. 7 shows a processing flow according to Example 5 of the present disclosure. In the Example 5, the control unit controls the acquisition unit according to the prestored parameters. The electroencephalograph system further includes a storage unit configured for storing the first acquisition parameter and the second acquisition parameter. Alternatively, the control unit includes the storage unit.

Specifically, as shown in FIG. 7, the electroencephalograph system performs the following steps.

S501: When no stimulation is applied (during non-stimulation), the acquisition unit 102 acquires the physiological electrical signals of the human brain according to the prestored first acquisition parameter. For example, the sampling rate (that is, the first acquisition frequency) is 1 kHz and the gain (that is, the first signal gain) is 100.

S502: The control unit 203 prepares to request or controls the stimulation unit 101 to apply stimulation, and adjusts the acquisition parameter of the acquisition unit 102 into the second acquisition parameter according to the prestored parameters. For example, the sampling rate (that is, the second acquisition frequency) is 16 kHz and the gain (that is, the second signal gain) is 1.

S503: The stimulation unit 101 applies stimulation, and the acquisition unit 102 acquires the physiological electrical signals of the brain according to the adjusted acquisition parameter during stimulation. That is, the physiological electrical signals of the brain are acquired according to the sampling rate of 16 kHz and the signal gain of 1.

S504: The stimulation unit 101 finishes stimulation and during non-stimulation, the control unit 203 restores the acquisition parameter of the acquisition unit 102, so that the acquisition unit 102 performs acquisition according to the first acquisition parameter with the sampling rate of 1 kHz and the gain of 100.

It can be seen from the above that, in the Example 5, the control unit 203 adjusts the acquisition parameters used during stimulation and non-stimulation according to the prestored parameters, which reduces the influence of noise aliasing and signal gain on the acquired signals during stimulation.

Example 6

Figure 8:
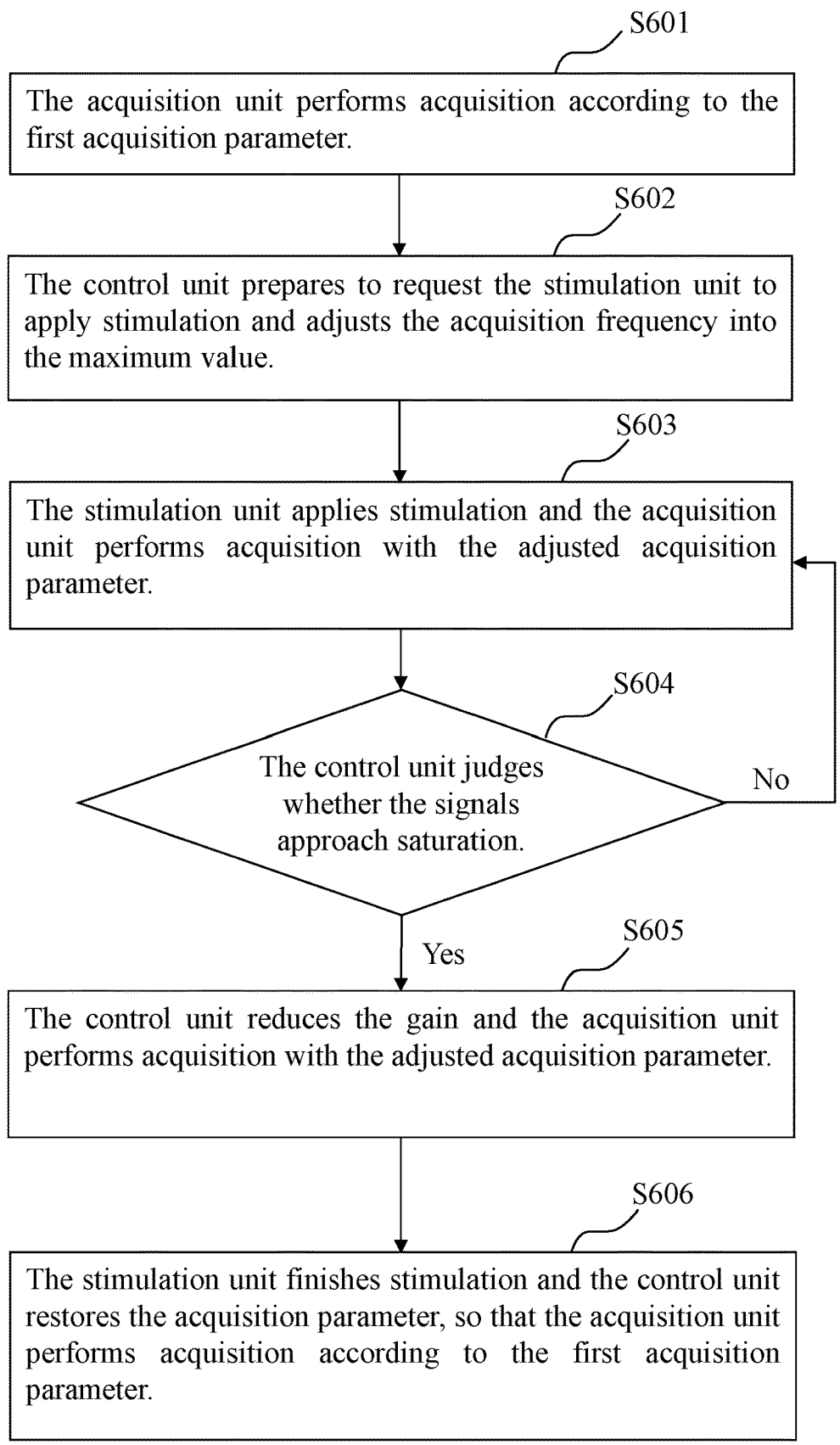
FIG. 8 shows a processing flow according to Example 6 of the present disclosure.

FIG. 8 shows a processing flow according to Example 6 of the present disclosure. Different from the Example 5, the acquisition parameters are adjusted according to real-time feedback in the Example 6. For example, the control unit 203 is further configured for adjusting the acquisition frequency of the acquisition unit into the second acquisition frequency when the control unit 203 determines that the stimulation unit intends to apply stimulation. When the stimulation unit applies the stimulation signal to the human body, the controlling, by the control unit, the acquisition unit to acquire the physiological electrical signals of the human brain according to the second acquisition parameter includes: judging whether the amplitude of the acquired signals exceeds a set threshold; and if yes, adjusting the signal gain of the acquisition unit into the second signal gain. In some embodiments of the present disclosure, the determining, by the control unit, that the stimulation unit intends to apply stimulation includes: determining, by the control unit, to request the stimulation unit to apply stimulation according to the physiological electrical signals of the brain acquired by the acquisition unit; or determining, by the control unit, that the stimulation unit intends to apply stimulation after the control unit receives a notification of the stimulation. The notification is sent by the stimulation unit or by a device other than the acquisition unit, the stimulation unit, and the control unit.

As shown in FIG. 8, the electroencephalograph system performs the following steps.

S601: When no stimulation is applied (during non-stimulation), the acquisition unit 102 acquires the physiological electrical signals of the human brain according to the first acquisition parameter. For example, the sampling rate (that is, the first acquisition frequency) is 1 kHz and the gain (that is, the first signal gain) is 100.

S602: The control unit 203 prepares to request or controls the stimulation unit 101 to apply stimulation, and adjusts the acquisition frequency into the acquisition frequency of the second acquisition parameter different from the first acquisition parameter. For example, the acquisition frequency is a maximum value supported by the system of the electroencephalograph device. In an alternative embodiment, the acquisition frequency of the second acquisition parameter can be other values higher than the first acquisition frequency.

S603: The acquisition unit 102 acquires the physiological electrical signals of the brain according to the adjusted acquisition parameter during the stimulation applied by the stimulation unit 101. For example, the acquisition is performed with a maximum sampling rate and a gain of 100.

S604: The control unit 203 judges in real time whether the signals acquired by the acquisition unit 102 approach saturation. For example, the control unit 203 judges whether the signal amplitude exceeds a set threshold. If yes, S605 is performed; otherwise, S603 is performed.

S605: The control unit 203 reduces the signal gain of the acquisition unit 102, that is, enables the acquisition unit 102 to perform acquisition with a gain lower than 100 (for example, 1) and a maximum sampling rate.

S606: The stimulation unit 101 finishes stimulation and the control unit 203 restores the acquisition parameter, that is, enables the acquisition unit 102 to perform acquisition according to the first acquisition parameter.

In the Example 6, the control unit 203 adjusts the parameters during stimulation. In an alternative embodiment, the acquisition unit 102 adjusts the parameters during stimulation.

Example 7

Figure 9:
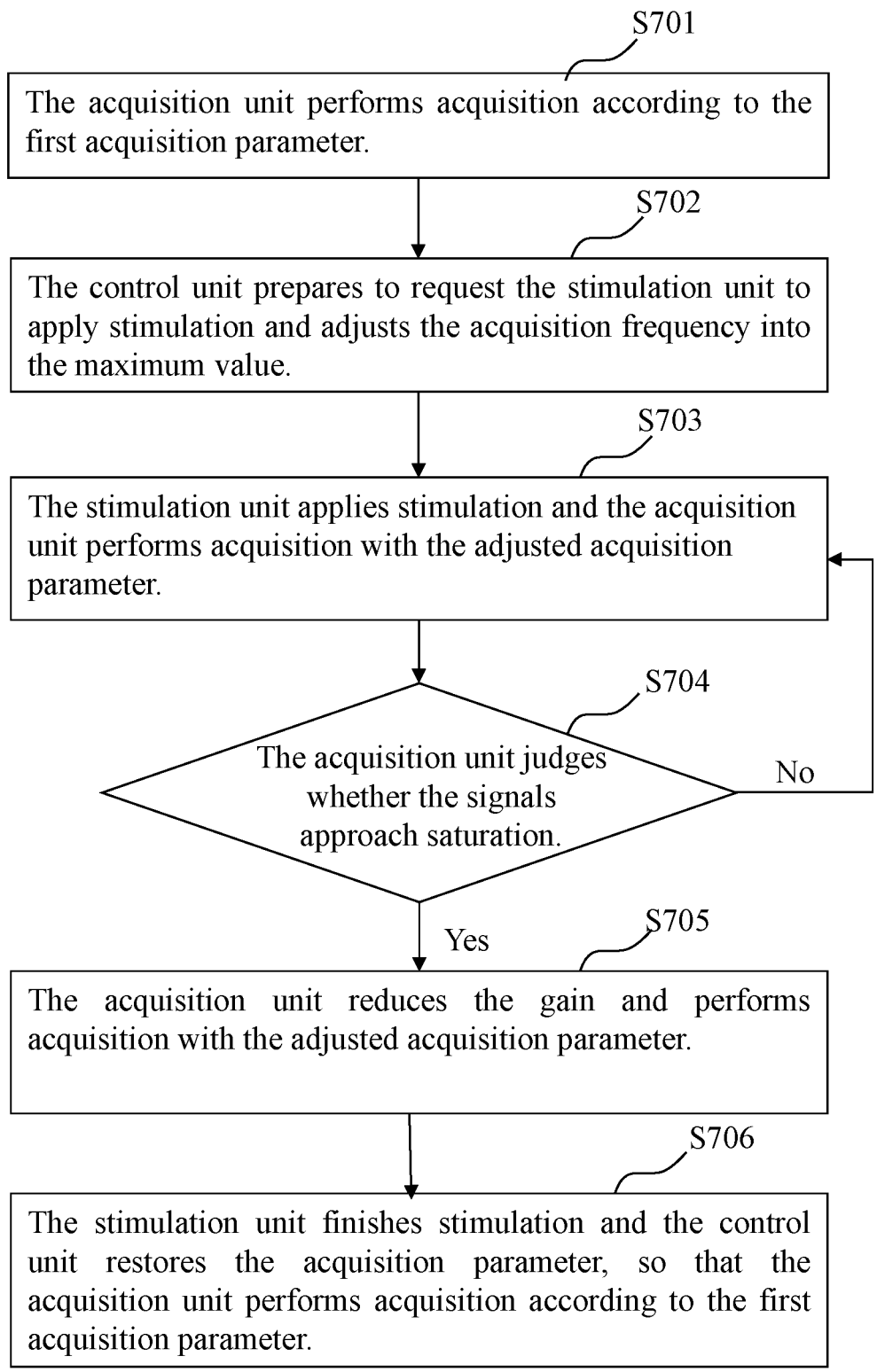
FIG. 9 shows a processing flow according to Example 7 of the present disclosure.

FIG. 9 shows a processing flow according to Example 7 of the present disclosure. Different from the Example 6, the acquisition unit 102 adjusts the parameters during stimulation in the Example 7. Specifically, as shown in FIG. 9, the electroencephalograph system performs the following steps.

S701: When no stimulation is applied (during non-stimulation), the acquisition unit 102 acquires the physiological electrical signals of the human brain according to the first acquisition parameter. For example, the sampling rate (that is, the first acquisition frequency) is 1 kHz and the gain (that is, the first signal gain) is 100.

S702: The control unit 203 prepares to request or controls the stimulation unit 101 to apply stimulation, and adjusts the acquisition frequency into the acquisition frequency of the second acquisition parameter different from the first acquisition parameter. For example, the acquisition frequency is a maximum value supported by the system of the electroencephalograph device. In an alternative embodiment, the acquisition frequency of the second acquisition parameter can be other values higher than the first acquisition frequency.

S703: The acquisition unit 102 acquires the physiological electrical signals of the brain according to the adjusted acquisition parameter during the stimulation applied by the stimulation unit 101. For example, the acquisition is performed with a maximum sampling rate and a gain of 100.

S704: The acquisition unit 102 judges in real time whether the acquired signals approach saturation. For example, the acquisition unit 102 judges whether the signal amplitude exceeds a set threshold. If yes, S705 is performed; otherwise, S703 is performed.

S705: The acquisition unit 102 reduces the signal gain, that is, performs acquisition with a gain lower than 100 (for example, 1) and a maximum sampling rate.

S706: The stimulation unit 101 finishes stimulation and the control unit 203 restores the acquisition parameter, that is, enables the acquisition unit 102 to perform acquisition according to the first acquisition parameter.

Figure 10:
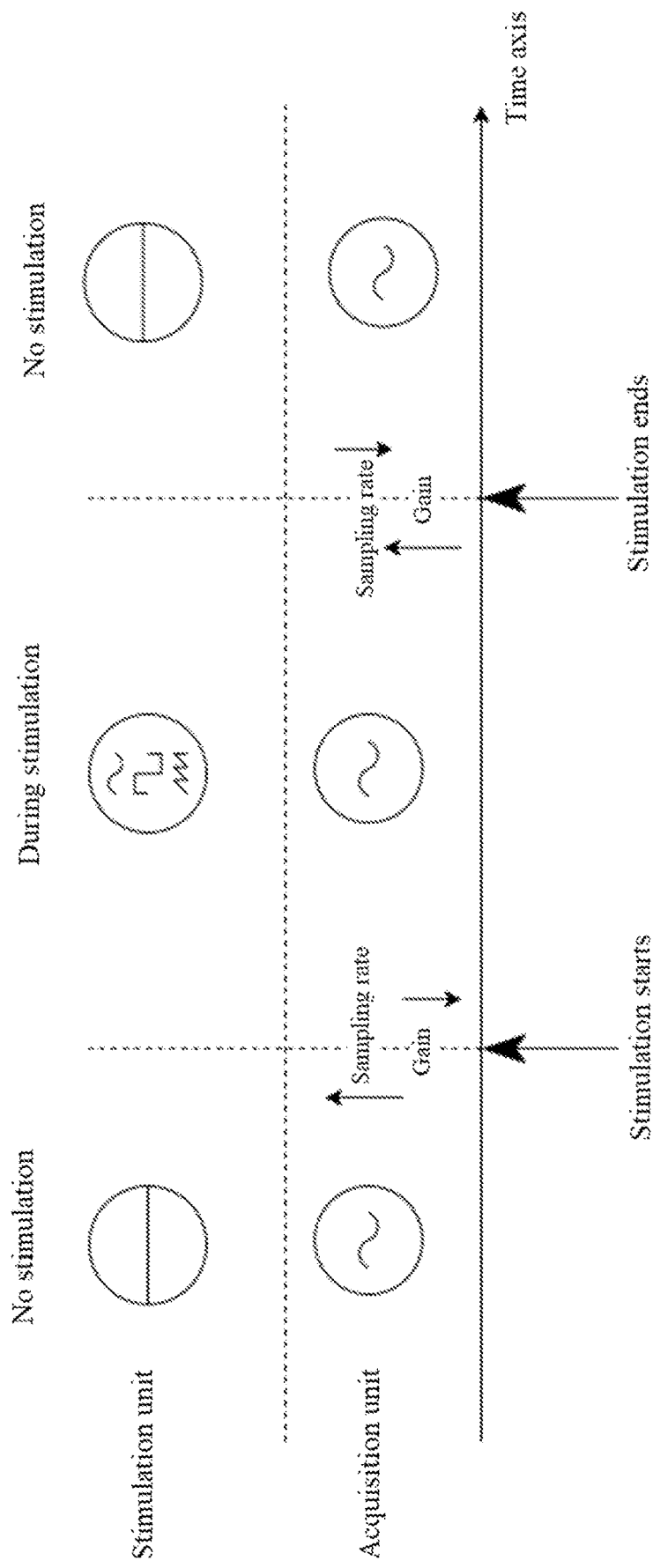
FIG. 10 is a schematic diagram illustrating the technical concept of the present disclosure.

The above examples describe in detail the electroencephalograph device and the electroencephalograph system of the present disclosure. According to the present disclosure, the acquisition unit adaptively adjusts the acquisition parameters when sensing that the stimulation unit generates and terminates the stimulation signal. The stimulation parameters can be adjusted by the system according to the real-time feedback of the acquired or stimulation signals during the acquisition or stimulation process, or can be adjusted according to a parameter adjustment scheme prestored in the system. FIG. 10 shows the principle of the specific implementation method, where the stimulation unit generates the stimulation signal to the human body and the acquisition unit acquires the physiological electrical signals of the human brain.

1. When No Stimulation Signal is Applied:

The acquisition unit acquires the electroencephalogram signals using the normal electroencephalogram acquisition parameter. The acquisition frequency is lower and the signal gain is higher than the circumstance where electrical stimulation is applied.

2. When the Stimulation is Applied:

The acquisition unit adjusts the acquisition parameters according to the predefined acquisition parameters or the real-time feedback of the acquisition unit, so that the sampling rate of the signals is increased and the gain of the acquired signals is reduced.

3. When the Stimulation Ends:

After the stimulation is over, the acquisition unit automatically restores the acquisition parameter in the non-stimulation state to acquire the electroencephalogram signals.

Persons skilled in the art should understand that, in addition to the aforementioned stimulation unit and acquisition unit, the electroencephalograph device and system can also include components related to stimulation, acquisition, and analysis, such as stimulation electrodes, acquisition electrodes, and information processing devices. Besides, in the above examples or embodiments, the present disclosure is exemplified with the sampling rate of 1 kHz and the gain of 100 as the first acquisition parameter during non-stimulation and with the sampling rate of 16 kHz and the gain of 1 as the second acquisition parameter during stimulation. However, the present disclosure is not limited to these specific values, and persons skilled in the art can set the first acquisition parameter and the second acquisition parameter according to the amplitude-frequency characteristics of the acquired signals and the system design constraints (such as volume or power consumption).

Through the above description of the embodiments, it is apparent to persons skilled in the art that the present disclosure can be implemented by means of software combined with hardware. Therefore, all or a part of the technical solutions of the present disclosure that make contributions to the prior art can be embodied in the form of a software product. The computer software product can be stored in a storage medium such as a read-only memory/random-access memory (ROM/RAM), a magnetic disk, or an optical disc, and contains several instructions to instruct a computer device (for example, a personal computer, a server, or a network device) to perform the methods described in the embodiments of the present disclosure or in some parts of the embodiments of the present disclosure.

Correspondingly, an embodiment of the present disclosure also provides a computer readable storage medium configured for storing computer readable instructions or programs. A processor executes the computer readable instructions or programs to perform operations that include the steps of the processing method described in any one of the above embodiments or examples. For instance, the processor executes the computer readable instructions to perform the following steps:

judging whether the stimulation unit applies the stimulation signal to the human body;

when the stimulation unit does not apply the stimulation signal to the human body, acquiring, by the acquisition unit, the physiological electrical signals of the human brain according to the first acquisition parameter; and when the stimulation unit applies the stimulation signal to the human body, acquiring, by the acquisition unit, the physiological electrical signals of the human brain according to the second acquisition parameter, the first acquisition parameter being different from the second acquisition parameter.

In some embodiments of the present disclosure, the first acquisition parameter includes the first acquisition frequency and/or the first signal gain; and the second acquisition parameter includes the second acquisition frequency and/or the second signal gain, the first acquisition frequency being lower than the second acquisition frequency and the second signal gain being lower than the first signal gain.

In some embodiments of the present disclosure, the processor executes the computer readable instructions to perform the following steps:

when determining that the stimulation unit intends to apply stimulation, adjusting the acquisition frequency of the acquisition unit into the second acquisition frequency; and when the stimulation unit applies the stimulation signal to the human body, judging whether the amplitude of the acquired signals exceeds the set threshold; and if yes, adjusting the signal gain of the acquisition unit into the second signal gain.

In some embodiments of the present disclosure, the determining that the stimulation unit intends to apply stimulation includes:

determining to request the stimulation unit to apply stimulation according to the physiological electrical signals of the brain acquired by the acquisition unit; or determining that the stimulation unit intends to apply stimulation according to a received notification of the stimulation.

In some embodiments of the present disclosure, the storage medium is, for example, an optical disc, a hard disk, a floppy disk, a flash memory, or a magnetic tape.

In addition, an embodiment of the present disclosure further provides a computer device including a memory and a processor. The memory is configured for storing one or more computer instructions or programs, and the processor executes the one or more computer instructions or programs to perform the processing method described in any one of the above embodiments or examples. For instance, the memory includes or has the above-mentioned computer readable storage medium. The computer device is, for example, a server, a desktop computer, a notebook computer, or a tablet computer.

The present disclosure has been described in detail above through various embodiments. Persons skilled in the art should understand that, the above descriptions are merely embodiments of the present disclosure, and are not intended to limit the protection scope of the present disclosure. Any equivalent changes made based on the embodiments of the present disclosure shall fall within the protection scope of the appended claims of the present disclosure.

What is claimed is:

1. An electroencephalograph device, comprising:
a stimulation unit, configured for generating a stimulation signal and apply the stimulation signal to a human body; and
an acquisition unit, configured for acquiring physiological electrical signals of a human brain, wherein
the acquiring, by the acquisition unit, the physiological electrical signals of the human brain comprises: when the stimulation unit does not apply the stimulation signal to the human body, acquiring, by the acquisition unit, the physiological electrical signals of the human brain according to a first acquisition parameter; and when the stimulation unit applies the stimulation signal to the human body, acquiring, by the acquisition unit, the physiological electrical signals of the human brain according to a second acquisition parameter,
wherein the first acquisition parameter is different from the second acquisition parameter, wherein the first acquisition parameter and the second acquisition parameter are the same parameter but have different values,
the first acquisition parameter comprises at least one of a first acquisition frequency and a first signal gain;
the second acquisition parameter comprises at least one of a second acquisition frequency and a second signal gain;
wherein the first acquisition frequency is lower than the second acquisition frequency and the second signal gain is lower than the first signal gain, wherein
the acquiring, by the acquisition unit, the physiological electrical signals of the human brain further comprises: when the acquisition unit determines that the stimulation unit intends to apply stimulation, adjusting, by the acquisition unit, the first acquisition frequency of the acquisition unit into the second acquisition frequency, wherein
when the stimulation unit applies the stimulation signal to the human body, the acquiring, by the acquisition unit, the physiological electrical signals of the human brain according to the second acquisition parameter comprises: judging, by the acquisition unit, whether an amplitude of the acquired signals exceeds a set threshold; and if yes, adjusting, by the acquisition unit, the first signal gain of the acquisition unit into the second signal gain.

2. The electroencephalograph device according to claim 1, further comprising a storage unit configured for storing the first acquisition parameter and the second acquisition parameter.

3. The electroencephalograph device according to claim 1, wherein the determining, by the acquisition unit, that the stimulation unit intends to apply stimulation comprises:
determining, by the acquisition unit, to request the stimulation unit to apply stimulation according to the acquired physiological electrical signals of the brain; or determining, by the acquisition unit, that the stimulation unit intends to apply stimulation after the acquisition unit receives a notification of the stimulation.

4. The electroencephalograph device according to claim 3, wherein the notification is sent by the stimulation unit or by a device other than the acquisition unit and the stimulation unit.

5. An electroencephalograph system, comprising the electroencephalograph device according to claim 1, wherein the system further comprises:
a control unit, configured for controlling the acquisition unit to acquire the physiological electrical signals of the human brain according to the first acquisition parameter when the stimulation unit does not apply the stimulation signal to the human body; and control the acquisition unit to acquire the physiological electrical signals of the human brain according to the second acquisition parameter when the stimulation unit applies the stimulation signal to the human body.

6. The electroencephalograph system according to claim 5, further comprising a storage unit configured for storing the first acquisition parameter and the second acquisition parameter.

7. The electroencephalograph system according to claim 5, wherein the control unit is further configured for adjusting the first acquisition frequency of the acquisition unit into the second acquisition frequency when the control unit determines that the stimulation unit intends to apply stimulation, wherein
when the stimulation unit applies the stimulation signal to the human body, the controlling, by the control unit, the acquisition unit to acquire the physiological electrical signals of the human brain according to the second acquisition parameter comprises: judging whether the amplitude of the acquired signals exceeds the set threshold; and if yes, adjusting the first signal gain of the acquisition unit into the second signal gain.

8. The electroencephalograph system according to claim 7, wherein the determining, by the control unit, that the stimulation unit intends to apply stimulation comprises:
determining, by the control unit, to request the stimulation unit to apply stimulation according to the physiological electrical signals of the brain acquired by the acquisition unit; or
determining, by the control unit, that the stimulation unit intends to apply stimulation after the control unit receives a notification of the stimulation.

9. The electroencephalograph system according to claim 8, wherein the notification is sent by the stimulation unit or by a device other than the acquisition unit, the stimulation unit, and the control unit.

10. A non-transitory computer readable storage medium, configured for storing computer readable instructions, wherein the electroencephalograph system according to claim 9 is included, wherein the electroencephalograph system further comprises a processor, the processor executes the computer readable instructions to perform following steps:
judging whether the stimulation unit applies the stimulation signal to the human body;
when the stimulation unit does not apply the stimulation signal to the human body, acquiring, by the acquisition unit, the physiological electrical signals of the human brain according to the first acquisition parameter; and
when the stimulation unit applies the stimulation signal to the human body, acquiring, by the acquisition unit, the physiological electrical signals of the human brain according to the second acquisition parameter.

11. The non-transitory computer readable storage medium according to claim 10, wherein the processor executes the computer readable instructions to perform following steps:
when determining that the stimulation unit intends to apply stimulation, adjusting the first acquisition frequency of the acquisition unit into the second acquisition frequency; and
when the stimulation unit applies the stimulation signal to the human body, judging whether the amplitude of the acquired signals exceeds the set threshold; and if yes, adjusting the first signal gain of the acquisition unit into the second signal gain.

12. The non-transitory computer readable storage medium according to claim 11, wherein the determining that the stimulation unit intends to apply stimulation comprises:
determining to request the stimulation unit to apply stimulation according to the physiological electrical signals of the brain acquired by the acquisition unit; or
determining that the stimulation unit intends to apply stimulation according to a received notification of the stimulation.

13. A computer device, comprising a memory and the processor, wherein the memory comprises the non-transitory computer readable storage medium according to claim 12, and the processor is configured for executing the computer readable instructions stored in the memory.

14. A computer device, comprising a memory and the processor, wherein the memory comprises the non-transitory computer readable storage medium according to claim 11, and the processor is configured for executing the computer readable instructions stored in the memory.

15. A computer device, comprising a memory and the processor, wherein the memory comprises the non-transitory computer readable storage medium according to claim 10, and the processor is configured for executing the computer readable instructions stored in the memory.

* * * * *